United States Patent

Kurihara et al.

Patent Number: 5,965,765
Date of Patent: Oct. 12, 1999

[54] PROCESS FOR PRODUCING α,β-UNSATURATED NITRILE

[75] Inventors: Shigeru Kurihara, Kurashiki; Hiroaki Muroya, Yokohama; Akihiko Sakamoto, Kawasaki, all of Japan

[73] Assignee: Asahi Kasei Kogyo Kabushiki Kaisha, Osaka, Japan

[21] Appl. No.: 09/101,321

[22] PCT Filed: Jan. 5, 1996

[86] PCT No.: PCT/JP96/00007

§ 371 Date: Jul. 2, 1998

§ 102(e) Date: Jul. 2, 1998

[87] PCT Pub. No.: WO97/25307

PCT Pub. Date: Jul. 17, 1997

[51] Int. Cl.⁶ .................................................. C07C 253/00
[52] U.S. Cl. ............................................................. 558/320
[58] Field of Search ................................................ 558/320

[56] References Cited

U.S. PATENT DOCUMENTS 5,288,473  2/1994  Shaw et al. ............................. 423/237

FOREIGN PATENT DOCUMENTS

| 40-2533 | 2/1965 | Japan . |
| 54-8655 | 4/1979 | Japan . |
| 6-211768 | 8/1994 | Japan . |
| 7-126237 | 5/1995 | Japan . |
| 8-27087 | 1/1996 | Japan . |

Primary Examiner—Johann Richter
Assistant Examiner—Joseph Murray
Attorney, Agent, or Firm—Pennie & Edmonds LLP

[57] ABSTRACT

A process for producing an α,β-unsaturated nitrile from propylene, isobutylene or tert-butyl alcohol in an industrial fluidized reactor with the step of feeding methanol and an oxygen-containing gas in the course of the whole contact time of the reactor and reacting unreacted ammonia with the methanol and the oxygen-containing gas, which can reduce the amount of unreacted ammonia without lowering the yield of the nitrile; and an industrial process of conducting the above production in an industrial fluidized reactor having an inner diameter of 3 m or above and filled with a molybdenum-bismuth catalyst supported on silica, which can prevent the feed opening of a dispersing nozzle for the methanol from clogging with molybdenum oxides to attain constant reduction in the amount of unreacted ammonia. The former is a process of catalytically reacting propylene, isobutylene or tert-butyl alcohol with ammonia and an oxygen-containing gas at high temperature in a gas phase by the use of a fluidized bed catalyst to form an α,β-unsaturated nitrile having the same number of carbon atoms as that of the starting propylene, isobutylene or tert-butyl alcohol, wherein methanol and an oxygen-containing gas are fed into the fluidized reactor at the positions corresponding to one-half to nine-tenths of the whole contact time from the point of feeding the starting materials through gas dispersing nozzles; and the latter is a process of producing an α,β-unsaturated nitrile as described above, wherein the methanol is fed together with steam through the same gas dispersing nozzle to thereby inhibit the catalyst from adhering to the dispersing nozzle and remove the catalyst adherent thereto.

7 Claims, 3 Drawing Sheets

PROCESS FOR PRODUCING α,β-UNSATURATED NITRILE

TECHNICAL FIELD

The present invention relates to a process for producing an α,β-unsaturated nitrile which comprises subjecting propylene, isobutylene, or tert-butyl alcohol to ammoxidation in a fluidized-bed reactor to produce an α,β-unsaturated nitrile having the same number of carbon atoms as propylene, isobutylene, or tert-butyl alcohol, wherein methanol and an oxygen-containing gas are fed in the course of the whole contact time under the same fluidized bed catalyst to cause ammoxidation reaction with unreacted ammonia to thereby diminish unreacted ammonia.

BACKGROUND ART

Fluidized-bed reactors have conventionally been employed extensively for producing an unsaturated nitrile by reacting ammonia, an oxygen-containing gas, and propylene, isobutylene, or tert-butyl alcohol by gas-phase catalytic reaction.

A fluidized-bed reactor usually has a gas dispersing device, a cooling coil, etc. in a lower part thereof. It further has a cyclone in an upper part thereof to conduct catalyst/gas separation.

The technique of feeding ammonia, methanol, and an oxygen-containing gas in the course of the whole contact time of a fluidized-bed reactor to cause ammoxidation reaction is known as disclosed in JP-B-54-8655. (The term "JP-B" as used herein means an "examined Japanese patent publication".) There is a description in the above reference to the effect that in a fluidized-bed reactor having an inner diameter of 2 inches and a height of 2 m, the ammoxidation reaction of methanol can be conducted without lowering the yield of acrylonitrile. In U.S. Pat. No. 5,288,473 is given an example in which a larger reactor for acrylonitrile is packed with about 18 t of a propylene ammoxidation catalyst. However, in a so-called commercial reactor having a diameter of 3 m or larger, production of the target α,β-unsaturated nitrile is inhibited because the methanol and the oxygen-containing gas which have been fed are mixed with the circulating fluidized bed catalyst and thus reach the region where ammoxidation reaction occurs between propylene, isobutylene, or tert-butyl alcohol and ammonia, and because methanol has a higher reaction rate than propylene, etc. Consequently, in industrial apparatuses, the feeding of methanol and an oxygen-containing gas results in a reduced yield of an α,β-unsaturated nitrile as compared with the case in which these ingredients are not fed. Sufficient investigations have not been made so far on measures for solving the above problem.

Furthermore, when an industrial fluidized-bed reactor having an inner diameter of 3 m or larger which employs a molybdenum-bismuth catalyst support on silica is used in such a manner that methanol and an oxygen-containing gas are fed thereto in the course of the whole contact time of the fluidized-bed reactor to cause ammoxidation reaction, then an oxide of molybdenum, which is a main constituent element of the catalyst, deposits on the feed openings of a methanol dispersing pipe with the lapse of time. This deposition finally results in clogging of the feed openings of the methanol dispersing pipe to pose an industrially serious problem that unreacted ammonia cannot be stably diminished. On measures for solving this problem also, sufficient investigations have not been made so far.

An object of the present invention is to provide a method of diminishing unreacted ammonia in an industrial fluidized-bed reactor used for producing an α,β-unsaturated nitrile through reaction of propylene, isobutylene, or tert-butyl alcohol, wherein unreacted ammonia is reacted with methanol and an oxygen-containing gas both fed in the course of the whole contact time of the fluidized-bed reactor to thereby diminish unreacted ammonia without lowering the yield of the α,β-unsaturated nitrile. Another object is to provide an industrial method of stably diminishing unreacted ammonia by preventing the clogging of the feed openings of a methanol dispersing pipe with a molybdenum oxide which clogging occurs when the above reaction is conducted in an industrial fluidized-bed reactor having an inner diameter of 3 m or larger and filled with a molybdenum-bismuth catalyst supported on silica.

DISCLOSURE OF THE INVENTION

The present inventors directed attention to the fact that in an industrial fluidizing-bed reactor for use in the production of an α,β-unsaturated nitrile, when methanol and an oxygen-containing gas are fed in the course of the whole contact time of the fluidized-bed reactor so as to react these ingredients with unreacted ammonia, then the methanol and oxygen-containing gas fed undergo reverse mixing with the fluidized catalyst circulating within the fluidized bed to reach the part to which propylene, isobutylene, and an oxygen-containing gas are fed to thereby considerably reduce the yield of an α,β-unsaturated nitrile. They further directed attention to the fact that by using methanol mixed with steam, the sublimation of a molybdenum oxide is accelerated. Based on the above, the present inventors made intensive studies. As a result, the present invention has been achieved.

Namely, the present invention relates to a process for producing an α,β-unsaturated nitrile which comprises catalytically reacting propylene, isobutylene, or tert-butyl alcohol with ammonia and an oxygen-containing gas at a high temperature in a gas phase by the use of a fluidized bed catalyst to produce an α,β-unsaturated nitrile having the same number of carbon atoms as propylene, isobutylene, or tert-butyl alcohol, wherein the reaction is conducted in a fluidized-bed reactor to which methanol and an oxygen-containing gas are fed through respective gas dispersing pipes at positions corresponding to from one half to nine tenths the whole contact time from the point of starting-material feeding, and which has one or more perforated structures having open area ratio of at least 60% disposed below and/or above the gas dispersing pipes. This invention further relates to the process for producing an α,β-unsaturated nitrile described above, characterized in that the methanol is fed together with steam through the same gas dispersing pipe to thereby prevent the catalyst from adhering to the dispersing pipe or remove the catalyst adherent thereto.

Due to the above, not only the conversion of methanol introduced into a conventional large reactor can be improved without causing a decrease in yield to thereby enable an α,β-unsaturated nitrile to be stably produced in a high yield, but also the nozzles of the methanol dispersing pipe can be prevented from being clogged.

The present invention will be explained below in detail.

FIG. 1 is a diagrammatic sectional view illustrating one example of reactors employed in prior art techniques.

FIG. 2 is a diagrammatic sectional view illustrating one example of reactors usable in the present invention. In FIGS. 1 and 2, numeral 1 denotes a reactor main body and 2 denotes a cooling coil. Numeral 3 denotes an olefin mixed gas dispersing pipe 3 for feeding a mixed gas comprising a mixture of propylene, isobutylene, or tert-butyl alcohol with ammonia, and 4 denotes an oxygen-containing gas feed pipe for feeding oxygen from a lower part of the reactor; the oxygen is introduced into the reactor through an oxygen-containing gas dispersing plate 5. Ammoxidation reaction is conducted in a fluidized-catalyst bed 6. Conditions for the reaction (operation conditions) are apparent to one skilled in the art; the molar ratio of the propylene, isobutylene, or tert-butyl alcohol used as a starting material to ammonia to oxygen is about 1/(1.0–1.3)/(1.7–2.3), and the reaction temperature is about from 400 to 500° C.

In the present invention, methanol or a methanol/steam mixture is fed through a methanol dispersing pipe 7 disposed in the course of the whole contact time of the fluidized-bed reactor and oxygen is fed through an oxygen-containing gas dispersing pipe 8 disposed likewise, as shown in FIG. 2. Thus, the unreacted ammonia present in that position is reacted with methanol and oxygen, that is, the ammoxidation reaction of methanol is conducted. Although the embodiment shown in FIG. 2 is a preferred embodiment in which the methanol dispersing pipe 7 is located above the oxygen-containing gas dispersing pipe 8, the reverse arrangement is possible.

The whole contact time of a fluidized-bed reactor is shown by the following equation.

$$\text{Whole contact time} = \frac{\text{Whole volume of catalyst layer during reaction (m}^3\text{)}}{\text{Amount of fed gases calculated for the reaction conditions (m}^3\text{/sec)}}$$

The term "amount of fed gases calculated for the reaction conditions" in the above equation means the actual flow rate calculated for the temperature and pressure under the reaction conditions (operation conditions) for the fluidized-bed reactor.

The positions of the methanol dispersing pipe 7 and the oxygen-containing gas dispersing pipe 8 are from one half to nine tenths, preferably from two thirds to nine tenths, the whole contact time. Due to this, the ammoxidation reaction of methanol proceeds efficiently.

The methanol dispersing pipe 7 and the oxygen-containing gas dispersing pipe 8 may be arranged in any manner as long as they have such a structure that methanol or a methanol/steam mixture comes into contact with oxygen and ammonia gas within the fluidized bed. Methanol and oxygen preferably are jetted face-to-face in the vertical direction and come into contact with each other. Consequently, the methanol dispersing pipe 7 and the oxygen-containing gas dispersing pipe 8, each having a pipe structure, each preferably comprises a pipe and nozzles 9 or 10 disposed thereon, whereby the gases can flow evenly throughout a section of the reactor at given flow rates. The gas feed nozzle openings of one of the dispersing pipes preferably face to those of the other pipe. More preferably, the nozzles of one of the pipes coincide in axis with those of the other.

The distance between the methanol feed openings (feed openings for methanol or a methanol/steam mixture) of the methanol dispersing pipe 7 and the oxygen-containing gas feed openings of the oxygen-containing gas dispersing pipe is not particularly limited. However, it is preferably from 10 to 200 mm. Those feed openings mean the tips of the nozzles 9 and 10. The length and inner diameter of each nozzle and the inner diameter of each of the dispersing pipes 7 and 8 are suitably selected according the size of the reactor, the number of nozzles, reaction conditions, etc.

The amounts of methanol and oxygen fed through these dispersing pipes 7 and 8 depend on as to what degree of the removal of unreacted ammonia should be attained, and also on the selectivities of the employed catalyst for methanol reaction and ammonia reaction. The amount of oxygen fed through the oxygen-containing gas dispersing pipe 8 is also not particularly limited as long as it is sufficient for reaction with methanol and ammonia. In the case where almost 100% of unreacted ammonia is to be removed, the ratio (molar ratio) of the unreacted ammonia to methanol to the oxygen fed through the oxygen-containing gas dispersing pipe 8 is preferably about 1/(1.0–2.5)/(1.0–2.5).

In the present invention, one or more perforated structures 11 having open area ratio of 60% or higher are disposed below and/or above the gas dispersing pipes. The open area ratio thereof, which enables fluidized catalyst particles to freely pass through, is preferably 80% or higher. Although there is no particular upper limit thereon, it may be 99%.

As shown in FIG. 2, each perforated structure 11 comprises one or more opening-forming members for forming many openings. Consequently, the open area ratio of a perforated structure disposed as shown in FIG. 2 can be expressed by the ratio of the total area $\Sigma s$ of the individual openings, each having an area of s when viewed from above, to the inner sectional area S of the reaction main body. That is, the open area ratio can be defined as $100 \times \Sigma s/S$ (%).

The perforated structures are not particularly limited in their constitution, and any structure may be used as long as it withstands high temperatures and a fluidized bed and is preferably made of a material inert to the reactions. Namely, each opening basically has any shape and each opening-forming member basically has any shape. Consequently, the individual openings may be the same or different in s or shape, and the opening-forming members may be the same or different in shape with respect to each of the units relating to the formation of s's. Examples of the shape of openings include polygons, e.g., triangle, rectangle, and hexagon, circle, and ellipse.

s is in the range of usually from 100 to 2,500 mm$^2$, preferably from 200 to 900 mm$^2$.

Examples of the material of the opening-forming members include metals, ceramics, etc. Examples of the basic shape thereof or the shape thereof prior to processing include linear, platy, and slit forms, etc.

A preferred perforated structure has a net or comb-like structure. The term comb-like structure means a net structure from which the lines in one of the two directions crossing at right angles have been removed so that the remaining opening-forming members are parallel to one another.

In the case where two or more perforated structures are used, the relationship between the perforated structures with respect to the relative position of openings or opening-forming members can be freely selected. For example, in the case where two comb-like perforated structure are used, examples of the arrangement thereof include one in which the opening-forming members of one of the perforated structures, when viewed from above, meet those of the other structure.

Specific examples of the perforated net structure include a wire screen. In this case, the open area ratio can be represented by $\{(b \times b')/(a \times a')\} \times 100$ (%) as shown in FIG. 3. The diameter of the opening-forming members, i.e., wires, is usually from 2 to 7 mm, preferably from 3 to 5 mm.

Although the number of such perforated structures is not particularly limited, it is preferably from 1 to about 8, especially preferably from 2 to 6.

The distance between each of the gas dispersing pipes for methanol and an oxygen-containing gas and the nearest perforated structure is preferably from 10 to 100 cm, or the interval between the perforated structures is preferably from 10 to 100 cm. That distance and that interval each is especially preferably from 40 to 60 cm. The term the distance between a perforated structure and a gas dispersing pipe means the distance between the lower end of the gas dispersing pipe and the upper end of the perforated structure when the gas dispersing pipe overlies the perforated structure, and means the distance between the upper end of the gas dispersing pipe and the lower end of the perforated structure when the gas dispersing pipe underlies the perforated structure. In the case where two or more perforated structures are used, the term interval between perforated structures means the distance between the lower end of an overlying perforated structure and the upper end of an underlying perforated structure.

As stated hereinabove, the present inventors found that feeding methanol and an oxygen-containing gas through respective gas dispersing pipes results in inhibition of the generation of the target α,β-unsaturated nitrile, because the gases fed undergo reverse mixing with the circulating fluidized bed catalyst to reach the region where propylene, isobutylene, or tert-butyl alcohol undergoes ammoxidation reaction with ammonia, and because methanol has a higher reaction rate than propylene, etc. According to the present invention, due to the use of one or more perforated structures, not only the reverse mixing is inhibited in producing an α,β-unsaturated nitrile, but also unreacted ammonia is simultaneously caused to efficiently undergo ammoxidation reaction with the fed methanol and oxygen-containing gas to thereby diminish unreacted ammonia.

The present inventors further found that the following phenomenon occurs in a method of diminishing unreacted ammonia in an industrial fluidized-bed reactor having an inner diameter of 3 m or larger, filled with a molybdenum-bismuth catalyst supported on silica, and used for producing an α,β-unsaturated nitrile through reaction of propylene, isobutylene, or tert-butyl alcohol which method comprises feeding methanol and an oxygen-containing gas in the course of the whole contact time of the fluidized-bed reactor to react these ingredients with unreacted ammonia. That is, molybdenum, which is a main constituent element of the silica-supported molybdenum-bismuth catalyst present in the flowing reaction gases, is reduced by the methanol fed through the methanol dispersing pipe and, during long-term operation, deposit as molybdenum dioxide on the inner wall of the methanol dispersing pipe. The deposit grows with the lapse of time and finally clogs the nozzles of the methanol dispersing pipe. As a result of intensive studies made by the present inventors in order to eliminate the above problem, they have found that the deposition of molybdenum dioxide can be prevented by feeding methanol mixed with steam. Namely, in an embodiment of the present invention, methanol is mixed with steam and the mixture is fed through the gas dispersing pipe 7 to conduct ammoxidation reaction to thereby stably diminish unreacted ammonia.

A homogeneous mixture of methanol and steam in a mixing ratio (steam/methanol (wt %)) of from 5 to 80%, preferably from 10 to 50%, is desirably fed through the methanol dispersing pipe. The steam to be mixed with methanol may have any properties as long as it has such a temperature as not to cause methanol condensation. Thus, the deposition of molybdenum dioxide in the methanol dispersing pipe, especially on the nozzles, can be prevented, and this in turn prevents the feed openings of the dispersing pipe from being clogged. As a result, ammoxidation reaction can be stably conducted.

DESCRIPTION OF SYMBOLS

1 . . . reactor main body, 2 . . . cooling coil, 3 . . . olefin mixed gas dispersing pipe, 4 . . . oxygen-containing gas feed pipe, 5 . . . oxygen-containing gas dispersing plate, 6 . . . fluidized-catalyst bed, 7 . . . methanol dispersing pipe, 8 . . . secondary oxygen-containing gas dispersing. pipe, 9 . . . nozzle, 10 . . . nozzle, 11 . . . perforated structure

BEST MODES FOR CARRYING OUT THE INVENTION

The present invention will be explained below in more detail by reference to Examples and Comparative Examples.

EXAMPLE 1

A reactor having an inner diameter of 3.7 m was used, and a silica-supported molybdenum-bismuth catalyst having particle diameters of from 10 to 100 μm and an average particle diameter of 60 μm was used.

Figure 1:
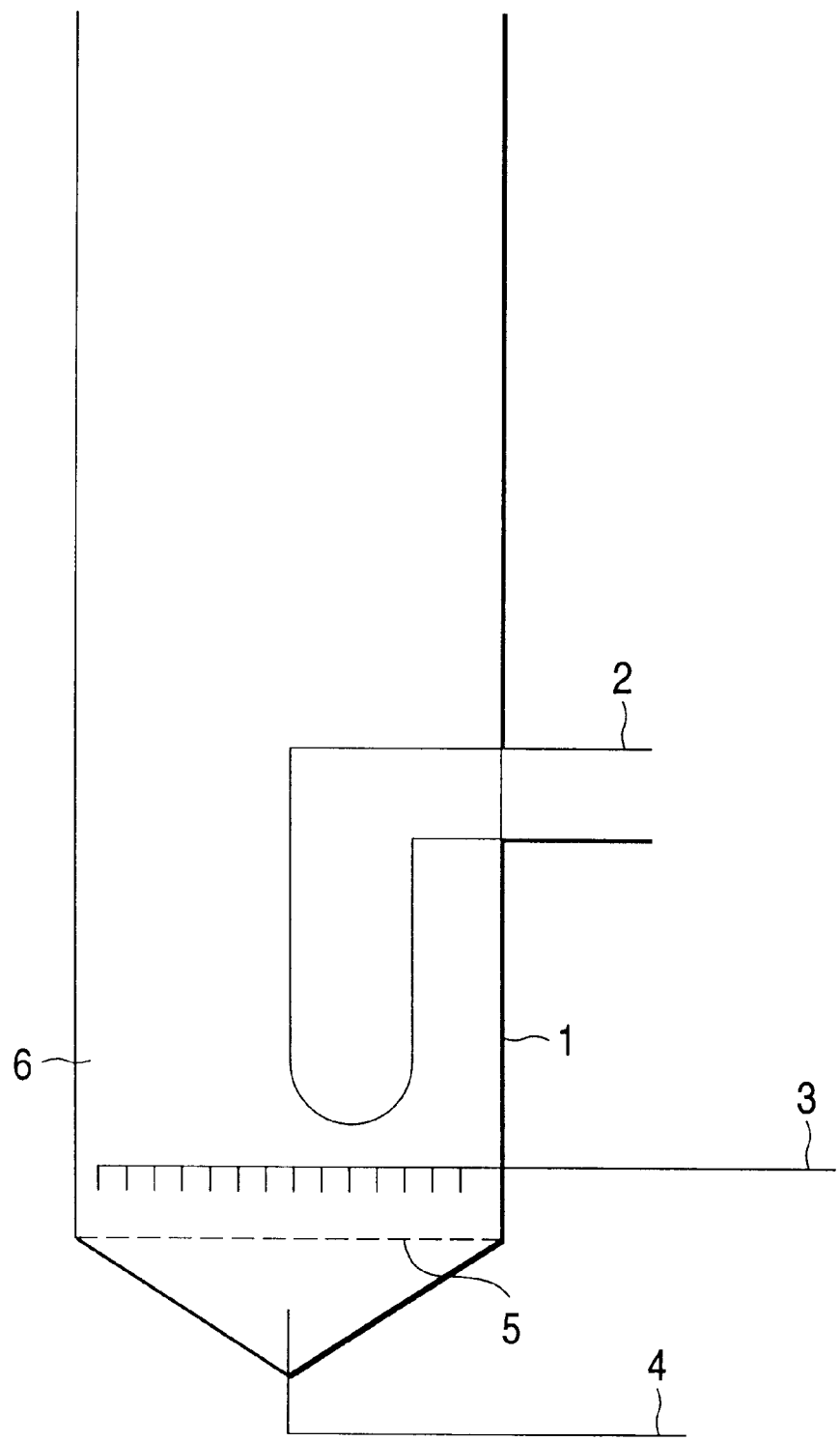
FIG. 1 is a schematic view illustrating one example of conventional reactors.
Figure 2:
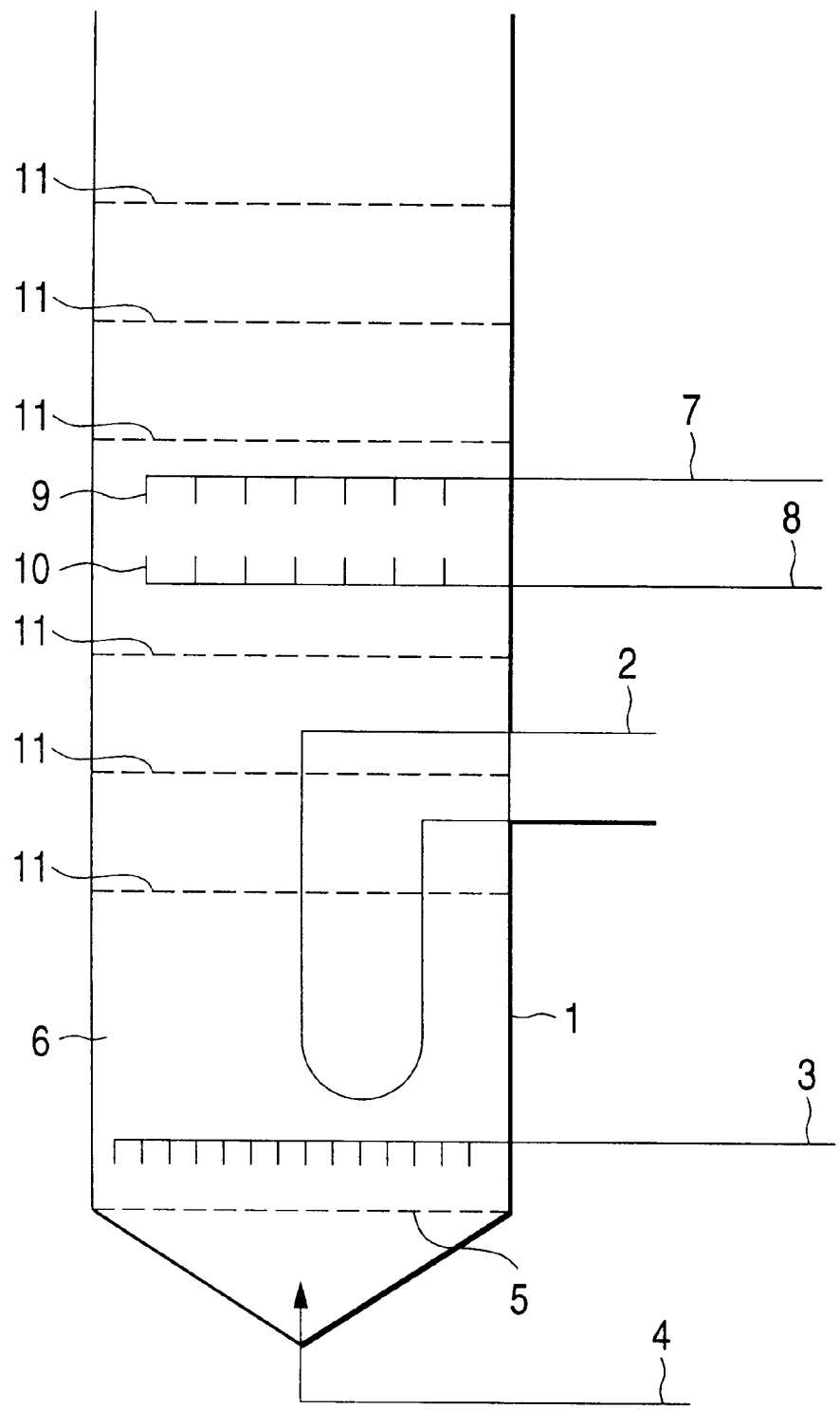
FIG. 2 is a schematic view illustrating one example of reactors usable in the present invention.
Figure 3:
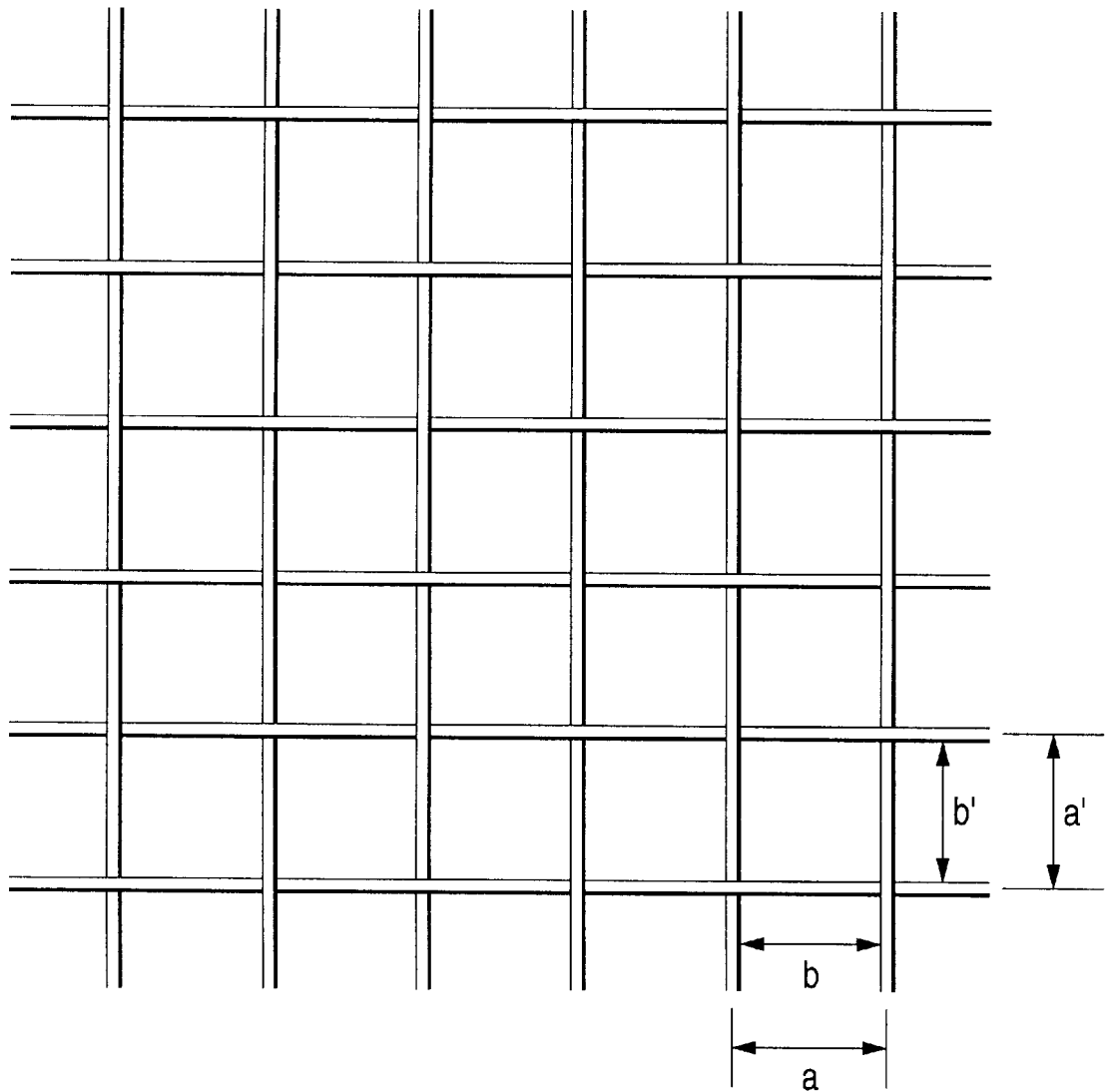
FIG. 3 is a view illustrating one example of the perforated structures used in the present invention.
Figure 4:
FIG. 4 is a cross sectional view illustrating one example of the perforated structure used in the present invention.

The catalyst was introduced into the reactor in such an amount as to result in a contact time for reaction gases of 4 seconds based on the height of the stationary catalyst bed. An air dispersing plate was disposed in a lower part of a fluidized bed, and a propylene/ammonia dispersing pipe was disposed above the openings of the plate. A methanol dispersing pipe and an air dispersing pipe were disposed at the position corresponding to a contact time of 3 seconds based on the height of the stationary catalyst bed. Furthermore, six metal screens having an opening size of 900 mm$^2$ (b=b'=30 mm in FIG. 3), a diameter of 3 mm (a=a'=33 mm in FIG. 3), and open area ratio of 82.6% were horizontally disposed in such a manner that three were disposed below the methanol dispersing pipe and the secondary air dispersing pipe at an interval of 0.5 m from the dispersing pipes and the remaining three were disposed above these pipes at an interval of 0.5 m. The reaction conditions used in this operation and the results of reaction are shown in Table 1.

COMPARATIVE EXAMPLE 1

A reactor having a diameter of 3.7 m was used in which the perforated structures shown in Example 1 were not disposed. A silica-supported molybdenum-bismuth catalyst having particle diameters of from 10 to 100 μm and an average particle diameter of 60 μm was used.

The catalyst was introduced into the reactor in such an amount as to result in a contact time for reaction gases of 4 seconds based on the height of the stationary catalyst bed. An air dispersing plate was disposed in a lower part of a fluidized bed, and a propylene/ammonia dispersing pipe was disposed above the openings of the plate. A methanol dispersing pipe and an air dispersing pipe were disposed at the position corresponding to a contact time of 3 seconds based on the height of the stationary catalyst bed.

The reaction conditions used in this operation and the results of reaction are shown in Table 1.

COMPARATIVE EXAMPLE 2

A reactor having a diameter of 3.7 m was used in which the perforated structures, methanol dispersing pipe, and air dispersing pipe shown in Example 1 were not disposed. A silica-supported molybdenum-bismuth catalyst having particle diameters of from 10 to 100 $\mu$m and an average particle diameter of 60 $\mu$m was used.

The catalyst was introduced into the reactor in such an amount as to result in a contact time for reaction gases of 4 seconds based on the height of the stationary catalyst bed. An air dispersing plate was disposed in a lower part of a fluidized bed, and a propylene/ammonia dispersing pipe was disposed above the openings of the plate to conduct reaction.

The reaction conditions used in this operation and the results of reaction are shown in Table 1.

TABLE 1

|  | Unit | Example | Comparative Example 1 | Comparative Example 2 |
|---|---|---|---|---|
| Whole contact time | sec | 4.0 | 4.0 | 4.0 |
| Methanol contact time | sec | 1.0 | 1.0 | 0.0 |
| Ammonia/propylene ratio | — | 1.1 | 1.1 | 1.1 |
| Air/propylene ratio | — | 9.4 | 9.4 | 9.4 |
| Methanol/propylene ratio | — | 0.12 | 0.12 | 0.0 |
| Secondary air/methanol ratio | — | 6.0 | 6.0 | 0.0 |
| Conversion of propylene | % | 99.8 | 99.8 | 99.7 |
| Conversion of methanol | % | 98.0 | 95.0 | — |
| Percentage of unreacted ammonia | % | 0 | 0 | 8.0 |
| Yield of acrylonitrile | % | 81.0 | 78.0 | 81.0 |
| Yield of prussic acid | % | 7.0 | 7.0 | 4.0 |

EXAMPLE 2

A reactor having a diameter of 3.7 m was used in which the same perforated structures as in Example 1 were disposed. A silica-supported molybdenum-bismuth catalyst having particle diameters of 10 to 100 $\mu$m and an average particle diameter of 60 $\mu$m was used.

The catalyst was introduced into the reactor in such an amount as to result in a contact time for reaction gases of 4 seconds based on the height of the stationary catalyst bed. An air dispersing plate was disposed in a lower part of a fluidized bed, and a propylene/ammonia dispersing pipe was disposed above the openings of the plate. A methanol dispersing pipe and an air dispersing pipe were disposed face-to-face at the position corresponding to a contact time of 3.2 seconds based on the height of the stationary catalyst bed, in such a manner that the distance between the methanol feed openings and the air feed openings was 20 mm. The reactor was operated over 13 days under the conditions of air/NH$_3$/C$_3$H$_6$=9.4/1.1/1.0, secondary air/methanol/C$_3$H$_6$= 0.77/0.096/1.0, and a steam/methanol mixing ratio of 35%. The results of this reaction included: percentage of unreacted ammonia =2% and conversion of methanol =97%, which were stably maintained throughout the 13 days. The methanol dispersing pipe had a constant pressure loss of 700 mmH$_2$O throughout the operation.

EXAMPLE 3

The same reactor and catalyst as in Example 2 were used. The catalyst was introduced into the reactor in such an amount as to result in a contact time for reaction gases of 4 seconds based on the height of the stationary catalyst bed. An air dispersing plate was disposed in a lower part of a fluidized bed, and a propylene/ammonia dispersing pipe was disposed above the openings of the plate. A methanol dispersing pipe and an air dispersing pipe were disposed face-to-face at the position corresponding to a contact time of 3.1 second based on the height of the stationary catalyst bed, in such a manner that the distance between the methanol feed openings and the air feed openings was 20 mm. The reactor was operated over 14 days under the conditions of air/NH$_3$/C$_3$H$_6$=9.0/1.1/1.0, secondary air/methanol/C$_3$H$_6$= 0.69/0.17/1.0, and a steam/methanol mixing ratio of 14%. The results of this reaction included: percentage of unreacted ammonia =0% and conversion of methanol =97.5%, which were stably maintained throughout the 14 days. The methanol dispersing pipe had a constant pressure loss of 1,300 mmH$_2$O throughout the operation.

COMPARATIVE EXAMPLE 3

The same reactor and catalyst as in Example 2 were used. The catalyst was introduced into the reactor in such an amount as to result in a contact time for reaction gases of 4 seconds based on the height of the stationary catalyst bed. An air dispersing plate was disposed in a lower part of a fluidized bed, and a propylene/ammonia dispersing pipe was disposed above the openings of the plate. A methanol dispersing pipe and an air dispersing pipe were disposed face-to-face at the position corresponding to a contact time of 3 seconds based on the height of the stationary catalyst bed, in such a manner that the distance between the methanol feed openings and the air feed openings was 20 mm. The reactor was operated over 5 days under the conditions of air/NH$_3$/C$_3$H$_6$=9.4/1.1/1.0 and secondary air/methanol/ C$_3$H$_6$= 0.96/0.19/1.0, using the methanol dispersing pipe for feeding methanol alone, i.e., without introducing steam thereinto. This reaction gave the following results. The percentage of unreacted ammonia and the conversion of methanol were 0% and 98%, respectively, in the beginning, and changed through the 5-day operation to 1% and 97.5%, respectively. The methanol dispersing pipe initially had a pressure loss of 1,000 mmH$_2$O, which increased to 1,500 mmH$_2$O.

COMPARATIVE EXAMPLE 4

The same reactor and catalyst as in Example 2 were used. The catalyst was introduced into the reactor in such an amount as to result in a contact time for reaction gases of 4 seconds based on the height of the stationary catalyst bed. An air dispersing plate was disposed in a lower part of a fluidized bed, and a propylene/ammonia dispersing pipe was disposed above the openings of the plate. A methanol dispersing pipe and an air dispersing pipe were disposed face-to-face at the position corresponding to a contact time of 3.1 second based on the height of the stationary catalyst bed, in such a manner that each pipe faced downward and the distance between the methanol feed openings and the air feed openings was 220 mm. The reactor was operated over 5 days under the conditions of air/NH$_3$/C$_3$H$_6$=9.4/1.1/1.0 and secondary air/methanol/C$_3$H$_6$=0.96/0.19/1.0, using the methanol dispersing pipe for feeding methanol alone, i.e., without introducing steam thereinto. This reaction gave the following results. The percentage of unreacted ammonia and the conversion of methanol were 0% and 98%, respectively, in the beginning, and changed through the 5-day operation to 1% and 96.5%, respectively. The methanol dispersing pipe initially had a pressure loss of 1,000 mmH$_2$O, which increased to 7,000 mmH$_2$O.

Values given in the Examples and Comparative Examples were obtained using the following equations.

$$\text{Whole contact time (sec)} = \frac{\text{Whole volume of catalyst layer during reaction (m}^3)}{\text{Amount of fed gases calculated for the reaction conditions (m}^3\text{/sec)}}$$

$$\text{Contact time from methanol feed openings (sec)} = \frac{\text{Volume of catalyst layer in methanol reaction zone during reaction (m}^3)}{\text{Amount of fed gases calculated for conditions (m}^3\text{/sec)}}$$

$$\text{Pressure loss of methanol dispersing pipe (mmH}_2\text{O)} = [(\text{Pressure at inlet of methanol dispersing pipe}) - (\text{Pressure of reactor just above methanol dispersing pipe})]$$

$$\text{Ammonia/propylene ratio} = \frac{\text{Number of moles of fed ammonia}}{\text{Number of moles of fed propylene}}$$

$$\text{Air/propylene ratio} = \frac{\text{Number of moles of fed air}}{\text{Number of moles of fed propylene}}$$

In the above equation, the term "number of moles of air" means the amount of air (Nm$^3$/HR) introduced through the oxygen-containing gas feed pipe 4 and converted to mol.

$$\text{Methanol/propylene ratio} = \frac{\text{Number of moles of methanol}}{\text{Number of moles of fed propylene}}$$

$$\text{Secondary air/methanol ratio} = \frac{\text{Number of moles of fed secondary air}}{\text{Number of moles of fed methanol}}$$

Conversion of propylene (%) =

$$\left(1 - \frac{\text{Number of moles of propylene at outlet of fluidized-bed reactor}}{\text{Number of moles of fed propylene}}\right) \times 100$$

Conversion of methanol (%) =

$$\left(1 - \frac{\text{Number of moles of methanol at outlet of fluidized-bed reactor}}{\text{Number of moles of fed methanol}}\right) \times 100$$

Percentage of unreacted ammonia (%) =

$$\frac{\text{Number of moles of ammonia at outlet of fluidized-bed reactor}}{\text{Number of moles of fed ammonia}} \times 100$$

Yield of acrylonitrile (%) =

$$\frac{\text{Number of moles of yielded acrylonitrile}}{\text{Number of moles of fed propylene}} \times 100$$

Yield of prussic acid (%) =

$$\frac{(\text{Number of moles of yielded prussic acid}) \times 1/3}{\text{Number of moles of fed propylene}} \times 100$$

POSSIBILITY OF INDUSTRIAL APPLICATION

According to the present invention, as shown in Example 1 given above, unreacted ammonia can be effectively diminished, without lowering the yield of an α,β-unsaturated nitrile, by reacting the unreacted ammonia with methanol and an oxygen-containing gas.

Furthermore, as shown in Examples 2 and 3 given above, unreacted ammonia can be stably diminished by reacting the unreacted ammonia with methanol and an oxygen-containing gas while preventing the feed openings of the methanol dispersing pipe from being clogged with a molybdenum oxide.

We claim:

1. A process for producing an α,β-unsaturated nitrile which comprises catalytically reacting propylene, isobutylene, or tert-butyl alcohol with ammonia and an oxygen-containing gas at a high temperature in a gas phase by the use of a fluidized bed catalyst to produce an α,β-unsaturated nitrile having the same number of carbon atoms as propylene, isobutylene, or tert-butyl alcohol, wherein the reaction is conducted in a fluidized-bed reactor to which methanol and an oxygen-containing gas are fed through respective gas dispersing pipes at positions corresponding to from one half to nine tenths the whole contact time from the a point of starting-material feeding, and which has one or more perforated structures having open area ratio of at least 60% disposed below and/or above the gas dispersing pipes.

2. The process for producing an α,β-unsaturated nitrile of claim 1, characterized in that the open area ratio is at least 80%.

3. The process for producing an α,β-unsaturated nitrile of claim 1 or 2, characterized in that the perforated structures each is a net or comb-like structure.

4. The process for producing an α,β-unsaturated nitrile of claim 1 or 2, characterized in that the distance between each of the gas discharging pipes and the nearest perforated structure is from 10 to 100 cm or the interval between the perforated structures is from 10 to 100 cm.

5. The process for producing an α,β-unsaturated nitrile of claim 1, characterized in that the methanol is fed together with steam through the same gas dispersing pipe to thereby prevent the catalyst from adhering to the dispersing pipe or remove the catalyst adherent thereto.

6. The process for producing an α,β-unsaturated nitrile of claim 5, characterized in that a gas dispersing pipe having nozzles is used for each of the methanol and the oxygen-containing gas, wherein the nozzles of one of the pipes coincide in axis with those of the other pipe and the distance between the methanol feed openings and the oxygen-containing gas feed openings is from 10 to 200 mm so that the methanol and the oxygen-containing gas are jetted face-to-face in the vertical direction and come into contact with each other.

7. The process for producing an α,β-unsaturated nitrile of claim 5 or 6, characterized in that the methanol and the steam are mixed in a steam/methanol ratio of from 5 to 80 wt % and fed through the same gas dispersing pipe.

* * * * *